(12) United States Patent
Lowe et al.

(10) Patent No.: US 9,987,248 B1
(45) Date of Patent: *Jun. 5, 2018

(54) METHOD FOR CANNABINOID TRANSDERMAL DELIVERY

(71) Applicants: Gary Allen Lowe, Bakersfield, CA (US); Vickie Lowe, Bakersfield, CA (US)

(72) Inventors: Gary Allen Lowe, Bakersfield, CA (US); Vickie Lowe, Bakersfield, CA (US)

( * ) Notice: Subject to any disclaimer, the term of this patent is extended or adjusted under 35 U.S.C. 154(b) by 108 days.

This patent is subject to a terminal disclaimer.

(21) Appl. No.: 15/340,088

(22) Filed: Nov. 1, 2016

Related U.S. Application Data

(63) Continuation of application No. 14/816,021, filed on Aug. 2, 2015, now Pat. No. 9,526,752.

(51) Int. Cl.
*A61K 36/00* (2006.01)
*A61K 31/352* (2006.01)
*A61K 47/44* (2017.01)
*A61K 9/00* (2006.01)
*A61K 31/05* (2006.01)
*A61K 36/185* (2006.01)

(52) U.S. Cl.
CPC .......... *A61K 31/352* (2013.01); *A61K 9/0014* (2013.01); *A61K 31/05* (2013.01); *A61K 36/185* (2013.01); *A61K 47/44* (2013.01)

(58) Field of Classification Search
CPC ...................................................... A61K 36/00
USPC ......................................................... 424/725
See application file for complete search history.

(56) References Cited

U.S. PATENT DOCUMENTS 9,156,809 B2 * 10/2015 Rieth ..................... C11B 9/008

* cited by examiner

*Primary Examiner* — Michael V Meller
(74) *Attorney, Agent, or Firm* — Williams Intellectual Property; Benjamin F. Williams

(57) ABSTRACT

A method for increased efficiency in transdermal delivery of cannabinoids wherein combination of cannabinoids with emu oil effects increased efficiency in delivery of cannabidinol and other cannabinoids to targeted areas in the hypodermis for therapeutic treatment therein, whereby inflammation and other symptomology is alleviated and convalescence assisted.

1 Claim, 1 Drawing Sheet

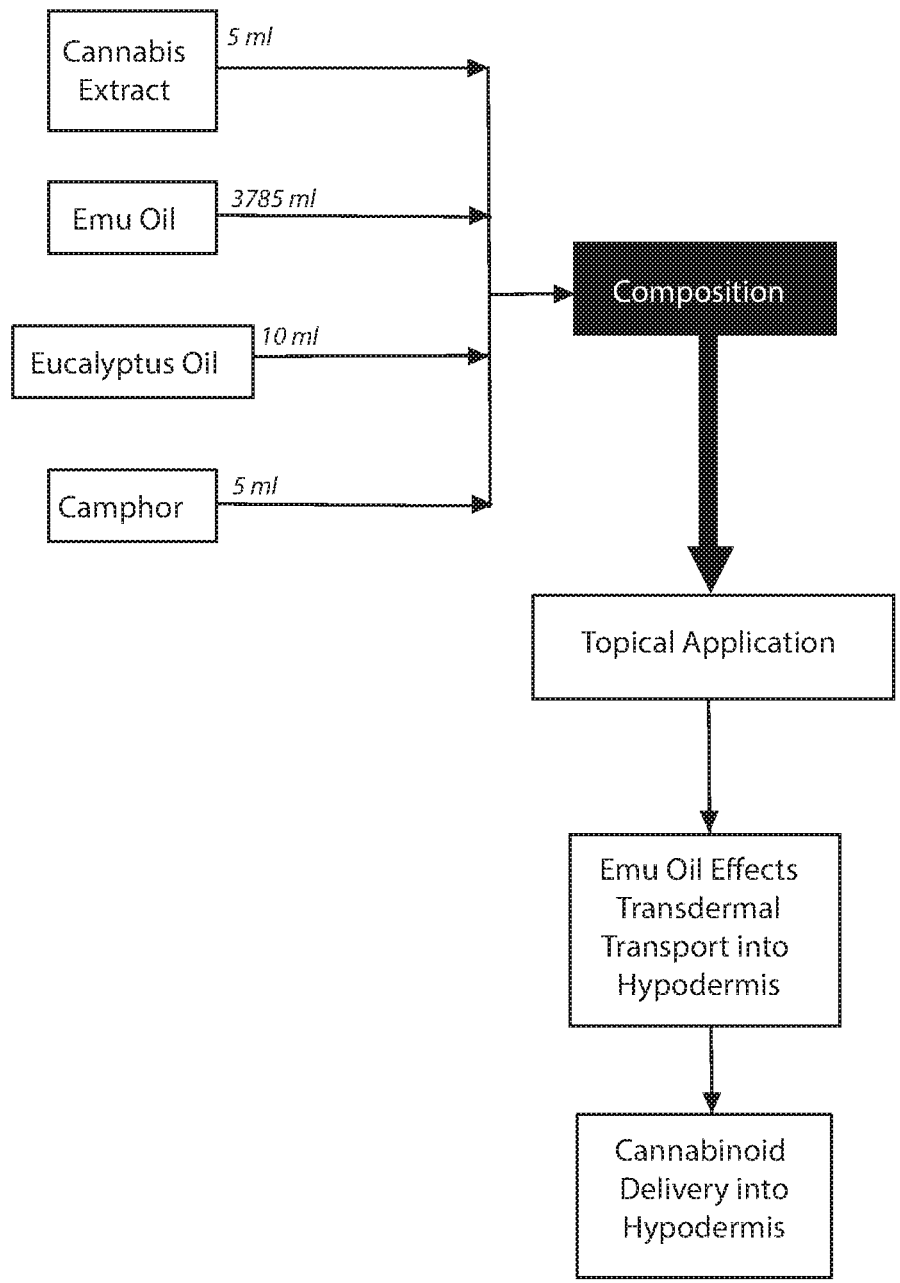

METHOD FOR CANNABINOID TRANSDERMAL DELIVERY

CROSS-REFERENCE TO RELATED APPLICATIONS

This continuing application for letters patent claims the benefit of nonprovisional application Ser. No. 14/816,021 filed on Aug. 2, 2015, which parent application claims the benefit of provisional application No. 62/115,631 filed on Feb. 12, 2015.

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Various types of compositions of cannabinoids are known in the prior art for use in therapeutic treatment of various disorders and discomforts, such as, for example, as an analgesic for treatment of arthralgia, neuralgia, inflammation, for inducing appetite, treatment of sleep apnea, hypertension, inhibiting growth of cancerous cells, among many other medical treatments and therapies. The pharmacological and therapeutic properties of cannabinoids are undergoing substantial discovery over the last few decades in the modern world, and are subject to a growing amount of scientific research. Cannabinoids, and their effect upon the eponymously named Endocannabinoid System in the human body, have remarkable properties in restoring the human body to health, regulating homeostasis, treating pain, inhibiting growth of cancerous cells, inducing appetite, assisting mood and sleep disorders, treating digestive disorders and other disorders and diseases. See, for example, the following included herein by reference:

Blake et. al. 2006. Preliminary assessment of the efficacy, tolerability and safety of a cannabis medicine (Sativex) in the treatment of pain caused by rheumatoid arthritis. *Rheumatology* 45: 50-52.

Ware et al. 2005. The medicinal use of cannabis in the UK: results of a nationwide survey. *International Journal of Clinical Practice* 59: 291-295.

Malfait et al. 2000. The nonpyschoactive cannabis constituent cannabidiol is an oral anti-arthritic therapeutic in murine. *Journal of the Proceedings of the National Academy of sciences* 97: 9561-9566

Sumariwalla et al. 2004. A novel synthetic, nonpsychoactive cannabinoid acid (HU-320) with anti-inflammatory properites in murine collagen-induced arthritis. *Arthritis & Rheumatism* 50: 985-998.

Neff et al. 2002. Preliminary observation with dronabinol in patients with intractable pruritus secondary to cholestatic liver disease. *American Journal of Gastroenterology* 97: 2117-2119.

Dvorak et al. 2003. Histamine induced responses are attenuated by a cannabinoid receptor agonist in human skin (PDF). *Inflammation Research* 25: 238-245.

Dvorak et al. 2003. Cannabinoid agonists attenuate capsaicin-induced responses in human skin. *Pain* 102: 283-288.

Szepietowski et al. 2005. Efficacy and tolerance of the cream containing structured physiological lipid endocannabinoids in the treatment of uremic pruritus: a preliminary study. *Acta Dermatovenerologic Croatica* (Croatia) 13: 97-103.

Paus et al. 2006. Frontiers in pruritus research: scratching the brain for more effective itch therapy. *Journal of Clinical Investigation* 116: 1174-1185.

Ofek et al. 2006. Peripheral cannabinoid receptor, CB2, regulates bone mass. *Proceedings of the National Academy of Sciences of the United States of America* 103: 696-701.

Itia Bab. 2007. Regulation of Skeletal Remodeling by the Endocannabinoid System. *Annals of the New York Academy of Sciences* 1116: 414-422.

Wade et al. 2006. Long-term use of a cannabis-based medicine in the treatment of spasticity and other symptoms of multiple sclerosis. *Multiple Sclerosis* 12: 639-645.

Wade et al. 2003. A preliminary controlled study to determine whether whole-plant cannabis extracts can improve intractable neurogenic symptoms. *Clinical Rehabilitation* 17: 21-29.

Meinck et al. 1989. Effects of cannabinoids on spasticity and ataxia in multiple sclerosis. *Journal of Neurology* 236: 120-122.

Denis Petro. 1980. Marijuana as a therapeutic agent for muscle spasm or spasticity. *Psychosomatics* 21: 81-85.

Pryce et al. 2003. Cannabinoids inhibit neurodegeneration in models of multiple sclerosis. *Brain* 126: 2191-2202.

de Lago et al. 2012. Cannabinoids ameliorate disease progression in a model of multiple sclerosis in mice, acting preferentially through CB(1) receptor-mediated anti-inflammatory effects. *Neuropharmacology*

Appendino et al. 2008. Antibacterial cannabinoids from *cannabis sativa*: a structure study. *Journal of Natural Products* 71: 1427-1430.

University of Pittsburgh Medical Center Press Release. May 21, 2006. "Marijuana-derived drug suppresses bladder pain in animal models."

Cecilia Hillard. 2000. Endocannabinoids and vascular function. *Journal of Pharmacology and Experimental Therapeutics*. 294: 27-32.

Kunos et al. 2000. Endocannabinoids as cardiovascular modulators. *Chemistry and Physics of Lipids* 108: 159-168.

Ribuot et al. 2005. Cardiac and vascular effects of cannabinoids: toward a therapeutic use? *Annales de Cardiologie et d'Angeiologie* (France) 54: 89-96.

Steven Karch. 2006. Cannabis and cardiotoxicity. *Forensic Science, Medicine, and Pathology*. 2: 13-18.

Steffens and Mach. 2006. Towards a therapeutic use of selective CB2 cannabinoid receptor ligands for atherosclerosis. *Future Cardiology* 2: 49-53.

Steffens et al. 2005. Low dose oral cannabinoid therapy reduces progression of atherosclerosis in mice. *Nature* 434: 782-786.

Pacher et al. 2005. Blood pressure regulation by endocannabinoids and their receptors (PDF). *Neuropharmacology* 48: 1130-1138.

ranjo Grotenhermen. 2006. Clinical pharmacodynamics of cannabinoids. In Russo et al (Eds) *Handbook of Cannabis Therapeutics*. Binghampton, N.Y.: Haworth Press.

Batkai et al. 2004. Endocannabinoids acting at cannabinoid-1 receptors regulate cardiovascular function in hypertension. *Circulation* 110: 1996-220.

Francois Mach. 2006. New anti-inflammatory agents to reduce atherosclerosis. *Archives of Physiology and Biochemistry* 112: 130-137.

Luvone et al. 2009. Cannabidiol: a promising drug for neurodegenerative disorders? *CNS Neuroscience & Therapeutics* 15: 65-75.

Sagredo et al. 2012. Cannabinoids: Novel Medicines for the Treatment of Huntington's Disease. *Recent Patents on CNS Drug Discovery* 7: 41-48.

Molina et al. 2011. Cannabinoid administration attenuates the progression of simian immunodeficiency virus. *AIDS Research and Human Retroviruses* 27: 585-592.

Ramirez et al. 2013. Attenuation of HIV-1 replication in macrophages by cannabinoid receptor 2 agonists. *Journal of Leukocyte Biology* 93: 801-810.

Riggs et al. 2012. A pilot study of the effects of cannabis on appetite hormones in HIV-infected adult men. *Brain Research* 1431: 46-52.

Gabbey et al. 2005. Endocannabinoids and liver disease-review. *Liver International* 25: 921-926.

Lavon et al. 2003. A novel synthetic cannabinoid derivative inhibits inflammatory liver damage via negative cytokine regulation. *Molecular Pharmacology* 64: 1334-1344.

Schnelle et al. 1999. Results of a standardized survey on the medical use of cannabis products in the German-speaking area. *Forschende Komplementarmedizin* (Germany) 3: 28-36.

Sylvestre et al. 2006. Cannabis use improves retention and virological outcomes in patients treated for hepatitis C. *European Journal of Gastroenterology & Hepatology*. 18: 1057-1063.

Marcu et al. 2010. Cannabidiol enhances the inhibitory effects of delta9-tetrahydrocannabinol on human glioblastoma cell proliferation and survival. *Molecular Cancer Therapeutics* 9: 180-189.

Preet et al. 2008. Delta9-Tetrahydrocannabinol inhibits epithelial growth factor-induced lung cancer cell migration in vitro as well as its growth and metastasis in vivo. *Oncogene* 10: 339-346.

Manuel Guzman. 2003. Cannabinoids: potential anticancer agents (PDF). *Nature Reviews Cancer* 3: 745-755.

Baek et al. 1998. Antitumor activity of cannabigerol against human oral epitheloid carcinoma cells. *Archives of Pharmacal Research:* 21: 353-356.

Carracedo et al. 2006. Cannabinoids induce apoptosis of pancreatic tumor cells via endoplasmic reticulum stress-related genes. *Cancer Research* 66: 6748-6755.

Michalski et al. 2008. Cannabinoids in pancreatic cancer: correlation with survival and pain. *International Journal of Cancer* 122: 742-750.

Ramer and Hinz. 2008. Inhibition of cancer cell invasion by cannabinoids via increased cell expression of tissue inhibitor of matrix metalloproteinases-1. *Journal of the National Cancer Institute* 100: 59-69.

Whyte et al. 2010. Cannabinoids inhibit cellular respiration of human oral cancer cells. *Pharmacology* 85: 328-335.

Leelawat et al. 2010. The dual effects of delta(9)-tetrahydrocannabinol on cholangiocarcinoma cells: anti-invasion activity at low concentration and apoptosis induction at high concentration. *Cancer Investigation* 28: 357-363.

Gustafsson et al. 2006. Cannabinoid receptor-mediated apoptosis induced by R(+)-methanandamide and Win55, 212 is associated with ceramide accumulation and p38 activation in mantle cell lymphoma. *Molecular Pharmacology* 70: 1612-1620.

Gustafsson et al. 2008. Expression of cannabinoid receptors type 1 and type 2 in non-Hodgkin lymphoma: Growth inhibition by receptor activation. *International Journal of Cancer* 123: 1025-1033.

Natalya Kogan. 2005. Cannabinoids and cancer. *Mini-Reviews in Medicinal Chemistry* 5: 941-952.

Scott et al. 2013. Enhancing the activity of cannabidiol and other cannabinoids in vitro through modifications to drug combinations and treatment schedules 33: 4373-4380.

Aviello et al. 2012. Chemopreventive effect of the non-psychotropic phytocannabinoid cannabidiol on experimental colon cancer. *Journal of Molecular Medicine.*

Ruiz et al. 1999. Delta-9-tetrahydrocannabinol induces apoptosis in human prostate PC-3 cells via a receptor-independent mechanism. *FEBS Letters* 458: 400-404.

Mimeault et al. 2003. Anti-proliferative and apoptotic effects of anandamide in human prostatic cancer cell lines. *Prostate* 56: 1-12.

Cafferal et al. 2010. Cannabinoids reduce ErbB2-driven breast cancer progression through Akt inhibition. *Molecular Cancer* 9: 196.

Guzman et al. 2000. Anti-tumoral action of cannabinoids: involvement of sustained ceramide accumulation and extracellular signal-regulated kinase activation. *Nature Medicine* 6: 313-319.

Guzman et al. 2003. Inhibition of tumor angiogenesis by cannabinoids. *The FASEB Journal* 17: 529-531.

Naftali et al. 2011. Treatment of Crohn's disease with cannabis: an observational study. *Journal of the Israeli Medical Association* 13: 455-458.

Izzo and Coutts. 2005. Cannabinoids and the digestive tract. *Handbook of Experimental Pharmacology* 168: 573-598.

Izzo et al. 2009. Non-psychotropic plant cannabinoids: new therapeutic opportunities from an ancient herb. *Trends in Pharmacological Sciences* 30: 515-527.

Lal et al. 2011. Cannabis use among patients with inflammatory bowel disease. *European Journal of Gastroenterology & Hepatology* 23: 891 896.

David Secko. 2005. Analgesia through endogenous cannabinoids. CMAJ 173.

Wallace et al. 2007. Dose-dependent effects of smoked cannabis on capsaicin-induced pain and hyperalgesia in healthy volunteers. *Anesthesiology* 107:785-96.

Cox et al. 2007. Synergy between delta9-tetrahydrocannabinol and morphine in the arthritic rat. *European Journal of Pharmacology* 567: 125-130.

Ethan Russo. 2004. Clinical endocannabinoid deficiency (CECD): Can this concept explain therapeutic benefits of cannabis in migraine, fibromyalgia, irritable bowel syndrome and other treatment-resistant conditions? *Neuroendocrinology Letters* 25: 31-39.

Burns and Ineck. 2006. Cannabinoid analgesia as a potential new therapeutic option in the treatment of chronic pain. *The Annals of Pharmacotherapy* 40: 251-260.

Fiz et al. 2011. Cannabis use in patients with fibromyalgia: Effect on symptoms relief and health-related quality of life. *PLoS One* 6.

chley et al. 2006. Delta-9-THC based monotherapy in fibromyalgia patients on experimentally induced pain, axon reflex flare, and pain relief. *Current Medical Research and Opinion* 22: 1269-1276.

Dale Gieringer. 2001. Medical use of cannabis: experience in California. In: Grotenhermen and Russo (Eds). *Can-* nabis and Cannabinoids: Pharmacology, Toxicology, and Therapeutic Potential. New York: Haworth Press: 153-170.

Porter and Jacobson. 2013. Report of a parnet survey of cannabidiol-enriched cannabis use in pediatric treatment-resistant epilepsy. Epilepsy & Behavior 29: 574-577.

Saundra Young, CNN.com. Aug. 7, 2013. "Marijuana stops child's severe seizures."

abusch et al. 2004. Delta-9-tetrahydrocannabinol improves motor control in a patient with musician's dystonia (PDF). Movement Disorders 19: 990-991.

Fox et al. 2002. Randomised, double-blind, placebo-controlled trial to assess the potential of cannabinoid receptor stimulation in the treatment of dystonia. Movement Disorders 17: 145-149.

Richter et al. 2002. Effects of pharmacological manipulations of cannabinoid receptors on severe dystonia in a genetic model of paroxysmal dyskinesia. European Journal of Pharmacology 454: 145-151.

Consroe et al. 1986. Open label evaluation of cannabidiol in dystonic movement disorders. International Journal of Neuroscience 30: 277-282.

Richter et al. 1994. (+)-WIN 55212-2, a novel cannabinoid agonist, exerts antidystonic effects in mutant dystonic hamsters. European Journal of Pharmacology 264: 371-377.

Rajavashisth et al. 2012. Decreased prevalence of diabetes in marijuana users. BMJ Open 2

Rajesh et al. 2010. Cannabidiol attenuates cardiac dysfunction, oxidative stress, fibrosis, and inflammatory and cell death signaling pathways in diabetic cardiomyopathy. Journal of the American College of Cardiology 56: 2115-2125.

El-Remessy et al. 2006. Neuroprotective and blood-retinal barrier preserving effects of cannabidiol in experimental diabetes. American Journal of Pathology 168: 235-244.

Lu et al. 2006. The cannabinergic system as a target for anti-inflammatory therapies. Current Topics in Medicinal Chemistry 13: 1401-1426.

Croxford and Yamamura. 2005. Cannabinoids and the immune system: Potential for the treatment of inflammatory diseases. Journal of Neuroimmunology 166: 3-18.

Wilsey et al. 2013. Low-dose vaporized cannabis significantly improves neuropathic pain. The Journal of Pain 14: 136-148.

Comelli et al. 2008. Antihyperalgesic effect of a Cannabis sativa extract in a rat model of neuropathic pain. Phytotherapy Research 22: 1017-1024.

Ware et al. 2010. Smoked cannabis for chronic neuropathic pain: a randomized controlled trial. CMAJ 182: 694-701.

Raman et al. 2004. Amyotrophic lateral sclerosis: delayed disease progression in mice by treatment with a cannabinoid. Amyotrophic Lateral Sclerosis & Other Motor Neuron Disorders 5: 33-39.

Carter et al. 2010. Cannabis and amyotrophic lateral sclerosis: hypothetical and practical applications, and a call for clinical trials. American Journal of Hospice & Palliative Medicine 27: 347-356.

Eubanks et al. 2006. A molecular link between the active component of marijuana and Alzheimer's disease pathology. Molecular Pharmaceutics 3: 773-777.

Marchalant et al. 2007. Anti-inflammatory property of the cannabinoid agonist WIN-55212-2 in a rodent model of chronic brain inflammation. Neuroscience 144: 1516-1522.

Campbell and Gowran. 2007. Alzheimer's disease; taking the edge off with cannabinoids? British Journal of Pharmacology 152: 655-662.

Ramirez et al. 2005. Prevention of Alzheimer's disease pathology by cannabinoids. The Journal of Neuroscience 25: 1904-1913.

Carley et al. 2002. Functional role for cannabinoids in respiratory stability during sleep. Sleep 25: 399-400.

Many medicinal uses for cannabinoids and cannabis extracts are effective via topical application of a salve or liniment wherein cannabinoids are absorbed by the body to local therapeutic effect. But what is needed is a composition of cannabinoids, odorous volatile compounds, and emu oil, that enables more effective transdermal delivery of cannabinoid into the hypodermis.

FIELD OF THE INVENTION

The present invention relates to a method for increased efficiency in cannabinoid transdermal delivery, wherein topical application of a composition of cannabinoids, odorous volatile compounds, and emu oil, enables more efficient transdermal delivery of cannabinoids to affected areas of the hypodermis for treatment of neuralgia, arthalgia, neuropathy, artritis, skin disorders, pruritus, gliomas, hypertension, dystonia among many other disorders, diseases, and discomforts effectively treated by hypodermal introduction of cannabinoids. The present invention further relates to a method for effecting transdermal delivery of cannabinoids by action of combination with emu oil. Odorous volatile compounds are further included to provide a pleasant odor to suppress the scent of cannabis extract during use of the composition.

SUMMARY OF THE INVENTION

The general purpose of the method for cannabinoid transdermal delivery, described subsequently in greater detail, is to provide a method for cannabinoid transdermal delivery which has many novel features that result in a composition of cannabinoids, odorous volatile compounds, and emu oil, and a method for cannabinoid transdermal delivery which is not anticipated, rendered obvious, suggested, or even implied by prior art, either alone or in combination thereof.

The present disclosure is directed towards a method for transdermally delivering cannabinoids to areas in the hypodermis for which therapeutic treatment is sought. Growing research supports the fact that cannabinoids have therapeutic and pharmacological effects useful in treatment of various diseases. Topical application of cannabis extract may alleviate symptoms and effect convalescence from said various diseases. The present composition improves upon topical salves having as ingredient cannabis extract by combination with a transdermal transporter, which enables more complete and efficient delivery of cannabinoids to the hypodermis.

Additional ingredients contemplated as part of this disclosure include odorous volatile compounds whereby a pleasant odor is released during use of the composition and the distinct smell of cannabis extract is thereby masked during use. In the example embodiment herein disclosed, said odorous volatile compounds are contemplated to include eucalyptus oil and camphor, which may also include therapeutic effects when topically applied.

The transdermal transporter included as part of this method is emu oil. Emu oil, which comprises v myristic acid, palmitic acid, palmitoleic acid, margaric acid, searic acid, elaidic acid, oleic acid, vaccenic acid, linoleic acid, linolenic acid, adachidie acid, and eicosenoic acid, has been shown to have therapeutic, anti-inflammatory properties itself, and to readily pass through the epidermis into underlying, subcutaneous tissue. The present composition enables penetration into the hypodermis and delivery of cannabinoids to desired areas whereat relief from neuralgia and inflammation is readily effected and convalescence and remediation thereby assisted.

The present method for cannabinoid transdermal delivery, therefore, includes topical application of the composition upon an area of epidermis proximal hypodermal arthralgia, neuralgia, or other symptomology, pain or discomfort. Cannabinoids are transported in the emu oil and delivered transdermally. The odorous volatile compounds evanesce as pleasant odors, whereby the scent of cannabis is masked.

Thus has been broadly outlined the more important features of the present composition of cannabinoids, odorous volatile compounds, and emu oil, and a method for cannabinoid transdermal delivery so that the detailed description thereof that follows may be better understood and in order that the present contribution to the art may be better appreciated.

For better understanding of the bottle attachable decanting aerator apparatus, its operating advantages and specific objects attained by its uses, refer to the accompanying drawings and description.

BRIEF DESCRIPTION OF THE DRAWING

Figures

FIG. 1 is a flow diagram view outlining example steps of an embodiment of the present composition and method.

DETAILED DESCRIPTION

With reference now to the drawings, and in particular FIG. 1 thereof, example of the instant composition of cannabinoids, odorous volatile compounds, and emu oil, and the method for cannabinoid transdermal delivery, employing the principles and concepts of the present composition of cannabinoids, odorous volatile compounds, and emu oil, and method for cannabinoid transdermal delivery will be described. The present composition of cannabinoids, odorous volatile compounds, and emu oil and method for cannabinoid transdermal delivery has been devised to enable infusion of cannabinoids to subcutaneous targets by topical application of the composition exteriorly upon proximal epidermis of a patient.

The present composition includes a mixture of emu oil and cannabis extract, together with odorous volatile compounds to perfume the mixture. The emu oil enables penetration of the cannabis extract through the epidermis into underlying subcutaneous tissue whereby anti-inflammatory and therapeutic benefits of cannabinoid exposure are effective. In an example embodiment set forth herein the composition is effected by volume:

3785 ml American Emu Oil
10 ml Eucalyptus Oil
5 ml Camphor
5 ml Cannabis extract (having approximately 50% cannabidiol (CBD)

The term "emu oil", as used herein throughout, is taken to include the subcutaneous fatty material extractable from the species *Dromiceius novaehollandiae*, which has been observed to transdermally transport to the hypodermis when topically applied [see, for example, *Experimental Study to Determine the AntiArthritic Activity of a New Emu Oil Formulation (EMMP)* by Ghosh and Whitehouse, Dec. 3, 1992].

The terms "cannabis extract" and "cannabinoids", as used herein throughout, are taken inclusive to include pharmaceutical compounds extractable from plants of the genus *Cannabis* generally, including cannabidiol ("CBD"), tetrahydrocannabinol ("THC"), and other variant organic, aromatic, lipophilic, hydrophilic, or hydrophobic, or other compounds extractable from said plants of the *Cannabis* genus.

In the example embodiment of the present composition set forth herein, the cannabis extract includes approximately 50% CBD, a non-psychoactive cannabinoid demonstrating therapeutic properties when introduced in vivo. In the example embodiment set forth herein, the composition includes approximately 0.015 to 1.5% CBD by volume, with a preferred embodiment of 0.0657% to 0.13% CBD by volume.

The present composition, therefore, enables transdermal transport of the CBD, and other cannabinoids, to the hypodermis for anti-inflammatory action and therapeutic treatment thereat. The eucalyptus and camphor lend a pleasant odor to the composition, and may further assist in transdermal transport into the hypodermis.

The present method for cannabinoid transdermal delivery, therefore, includes extraction of cannabinoids from a plant of the genus *Cannabis*, or otherwise synthetically preparing said cannabinoids in the laboratory from a suitable substrate. In the example embodiment herein set forth, the cannabinoids are extracted by carbon dioxide extraction from plants of the genus *Cannabis*; species and subspecies of the *Cannabis* plant having high CBD proportions are preferable.

The cannabis extract is then mixed with emu oil and odorous volatile compounds, such as, for example eucalyptus oil and camphor. The resulting liniment is topically applicable to a patient's epidermis. Cannabinoids are transported transdermally by action of the emu oil through the skin and thereby delivered to targeted areas and introduced into the hypodermis and bloodstream.

What is claimed is:

1. A method for cannabinoid transdermal delivery to a human or animal in need thereof of a composition of cannabis, eucalyptus oil and emu oil consisting essentially of the steps of:

topically applying a composition of cannabis extract, eucalyptus oil and emu oil to the epidermis of the human of animal;

thereby delivering cannabinoids hypodermally with increased efficiency as a result of action of the emu oil absorbing into the hypodermis of the human or animal and transporting cannabinoids therein to the human or animal;

and volatilizing odorous volatile compounds from the composition to mask the scent of the cannabis extract.

* * * * *